United States Patent
Wirth et al.

(10) Patent No.: US 9,504,936 B2
(45) Date of Patent: Nov. 29, 2016

(54) METHOD OF PACKING CHROMATOGRAPHIC COLUMNS

(75) Inventors: Mary Jean Wirth, West Lafayette, IN (US); Sampath Ranasinghe Kodithuwakkuge, West Lafayette, IN (US); Charu Yerneni, West Lafayette, IN (US); Robert Birdsall, West Lafayette, IN (US); Tharanga Ranasinghe Kodituwakkuge, legal representative, Athumgiriya (LK)

(73) Assignee: Purdue Research Foundation, West Lafayette, IN (US)

( * ) Notice: Subject to any disclaimer, the term of this patent is extended or adjusted under 35 U.S.C. 154(b) by 0 days.

(21) Appl. No.: 13/639,165

(22) PCT Filed: Apr. 5, 2011

(86) PCT No.: PCT/US2011/031234
§ 371 (c)(1),
(2), (4) Date: Jan. 15, 2013

(87) PCT Pub. No.: WO2011/127044
PCT Pub. Date: Oct. 13, 2011

(65) Prior Publication Data
US 2013/0193051 A1    Aug. 1, 2013

Related U.S. Application Data

(60) Provisional application No. 61/321,098, filed on Apr. 5, 2010.

(51) Int. Cl.
*B01D 15/20* (2006.01)
*G01N 30/56* (2006.01)
(Continued)

(52) U.S. Cl.
CPC ............ *B01D 15/206* (2013.01); *B01J 20/283* (2013.01); *G01N 30/56* (2013.01); *B01D 15/168* (2013.01);
(Continued)

(58) Field of Classification Search
CPC .... B01D 15/10; B01D 15/20; B01D 15/206; B01D 15/22; B01D 15/26; G01N 30/02; G01N 30/48; G01N 30/482; G01N 30/56; G01N 30/60; G01N 2030/562; G01N 2030/565; G01N 2030/524; G01N 2030/525; G01N 2030/521; G01N 2030/022; B01J 20/10; B01J 20/103; B01J 20/3092
See application file for complete search history.

(56) References Cited

U.S. PATENT DOCUMENTS 4,059,523 A * 11/1977 Mochizuki et al. ........ 210/198.2
4,175,037 A    11/1979 Benney et al.
(Continued)

FOREIGN PATENT DOCUMENTS

| JP | 11-044681 | 2/1999 |
| JP | 2006-181472 | 7/2006 |
| WO | WO 03/068402 | 8/2003 |

OTHER PUBLICATIONS

Wirth, Mary J., "Slip Flow Star", www.theanalyticalscientist.com, 3 Pages.
(Continued)

*Primary Examiner* — Katherine Zalasky
(74) *Attorney, Agent, or Firm* — McCarter & English, LLP

(57) ABSTRACT

Improved methods for packing a chromatographic column and columns packed by these methods are provided. The methods include introducing a packing material into a chromatographic column, while simultaneously ultrasonicating and applying pressure to the packing material to form a packed column with radial homogeneity.

24 Claims, 9 Drawing Sheets

(51) Int. Cl.
*G01N 30/50* (2006.01)
*G01N 30/52* (2006.01)
B01J 20/10 (2006.01)
B01J 20/283 (2006.01)
*B01J 20/30* (2006.01)
*B01D 15/26* (2006.01)
*B01D 15/16* (2006.01)
*B01D 15/30* (2006.01)
*B01D 15/32* (2006.01)
*G01N 30/88* (2006.01)

(52) U.S. Cl.
CPC .......... *B01D 15/305* (2013.01); *B01D 15/325* (2013.01); *G01N 2030/562* (2013.01); *G01N 2030/565* (2013.01); *G01N 2030/8831* (2013.01)

(56) References Cited

U.S. PATENT DOCUMENTS

| | | | |
|---|---|---|---|
| 4,305,275 A * | 12/1981 | Firth | B01D 15/206 73/19.02 |
| 4,352,570 A * | 10/1982 | Firth | B01D 15/206 241/175 |
| 4,985,143 A * | 1/1991 | Freeman et al. | 210/198.2 |
| 5,169,522 A * | 12/1992 | Shalon et al. | 210/198.2 |
| 5,919,368 A * | 7/1999 | Quinn et al. | 210/635 |
| 5,935,429 A * | 8/1999 | Liao et al. | 210/198.2 |
| 6,095,202 A * | 8/2000 | Colon et al. | 141/34 |
| 6,846,410 B2 * | 1/2005 | McNeff et al. | 210/198.2 |
| 7,101,477 B1 * | 9/2006 | Willis et al. | 210/198.2 |
| 2003/0089662 A1* | 5/2003 | Hofmann | 210/656 |
| 2003/0146159 A1 | 8/2003 | Guiochon | |
| 2005/0269264 A1* | 12/2005 | Fermier et al. | 210/635 |
| 2006/0144770 A1* | 7/2006 | Granger et al. | 210/198.2 |
| 2007/0181501 A1* | 8/2007 | Hoffmann et al. | 210/656 |
| 2007/0189944 A1* | 8/2007 | Kirkland et al. | 423/118.1 |
| 2009/0152201 A1* | 6/2009 | Wirth et al. | 210/656 |
| 2010/0224543 A1* | 9/2010 | Ellis et al. | 210/198.2 |
| 2011/0186731 A1* | 8/2011 | Van Els | G01N 30/463 250/288 |
| 2011/0226990 A1* | 9/2011 | Glennon et al. | 252/184 |

OTHER PUBLICATIONS

Reynolds, Kimberly J., et al., "Submicron Sized Organo-Silica Spheres for Capillary Electrochromatography", Journal of Liquid Chromatography & Related Technology, 2000, vol. 23, No. 1, pp. 161-173.

Ludtke, Silke, et al., "Application of 0.5-μm porous silanized silica beads in electrochromatography", Journal of Chromatography A, 1997, vol. 786, pp. 229-235.

Cabooter, Deirdre, et al., "Kinetic plot and particle size distribution analysis to discuss the performance limits of sub-2 μm and supra-2 μm particle columns", Journal of Chromatography A, 2008, vol. 1204, pp. 1-10.

Patel, Kamlesh, D., et al., "In-Depth Characterization of Slurry Packed Capillary Columns with 1.0 μm Nonporous Particles Using Reversed-Phase Isocratic Ultrahigh-Pressure Liquid Chromatography", Oct. 1, 2004, Analytical Chemistry, vol. 76, No. 19, pp. 5777-5786.

Gritti, Fabrice, et al., "Non-Invasive Measurement of Eddy Diffusion in Very Efficient Liquid Chromatography Columns Packed with Sub-3 μm Shell Particles", Dec. 1, 2010, Chemical Engineering Science, vol. 65, No. 23, pp. 6327-6340.

Gritti, Fabrice et al., "Relationship Between Trans-column Eddy Diffusion and Retention in Liquid Chromatography: Theory and Experimental Evidence", Oct. 8, 2010, Journal of Chromatography, vol. 1217, No. 41, pp. 6350-6365.

Supplementary European Search Report relating to co-pending counterpart of European Application No. 11766589, dated Jan. 26, 2015.

* cited by examiner 1 cm

US 9,504,936 B2

METHOD OF PACKING CHROMATOGRAPHIC COLUMNS

RELATED APPLICATIONS

This application is a §371 of International Application No. PCT/US11/31234, filed Apr. 5, 2011, which claim priority to U.S. Provisional Application No. 61/321,098, which was filed on Apr. 5, 2010,both of which are incorporated herein by reference in their entireties for all purposes.

FIELD OF THE INVENTION

The present disclosure relates to chromatographic columns and methods of packing chromatographic columns. More particularly, the disclosure relates to improved methods for uniformly packing chromatographic columns.

BACKGROUND

Chromatography may generally be used to separate compounds from a mixture. For example, in liquid chromatography, chromatography relies on compounds having a different distribution between solid particles in a stationary phase of a column and a liquid phase that is passed through the column. For ideal utilization of chromatography, the column packing material needs to be uniformly packed to provide a consistent path length for the separations to occur. A specific compound's affinity for the column packing material compared to its affinity for the mobile phase passing through the column determines the amount of time that the compound resides inside the column. After the compounds exit the column, they may be either individually detected (e.g. analytical liquid chromatography) or individually collected (e.g. preparative liquid chromatography). For the chromatographic separations to be carried out efficiently, the column packing material must be uniformly dispersed in the column with no gaps or cracks that would create re-mixing of the separated compounds.

The use of particles smaller than 2 µm in diameter has improved the performance of chromatographic separations (*J. Chromatog.* 1127: 60-69, 2006). A significant limitation to the chromatographic performance of sub-2 µm particles is the difficulty in achieving uniform packing; packed columns exhibit radial heterogeneity in packing, which deteriorates performance. This effect is called eddy diffusion. For example, a 100 µm inner diameter (i.d.) column of packed silica particles exhibits a contribution of 1.0 µm to the length-normalized peak variance (commonly called height equivalent to a theoretical plate) due to eddy diffusion (*Anal. Chem.* 76: 5777-5786, 2004). If the silica particles could be packed uniformly, i.e., with radial homogeneity, then separation performance would be expected to continue to improve as the particles decreased in size. Such improvements would be valuable, especially for protein and peptide separations, where there is a demand for separating mixtures of thousands of components, resolving very similar isoforms of a single protein, or determining the purity of therapeutic monoclonal antibodies. This improvement in packing would enable the commercial use of submicrometer particles for these and other separations. Silica particles have been successfully packed with virtually crystalline order in capillaries by using submicrometer, nonporous silica particles that have a narrow size distribution (*Langmuir* 20: 2033-2035, 2004). The limitation with this method is that there are usually gaps where the material meets the capillary wall, obviating any improvements in performance, and the packing procedure takes days.

BRIEF SUMMARY OF THE INVENTION

A method for packing a chromatographic column is presented, the method comprising the steps of a) introducing a packing material into a chromatographic column; b) ultrasonicating the chromatographic column; and c) applying pressure to the packing material, wherein steps a)-c) are performed simultaneously and wherein a packed chromatographic column with an eddy diffusion term of less than 1 µm is formed.

Also provided is a packed column prepared by the disclosed method, the column comprising uniformly packed chromatography material exhibiting no cracks, uninterrupted contact between the inner surface of the column and the chromatography material, and an eddy diffusion term of less than 1 µm.

DETAILED DESCRIPTION

Methods have been developed for improved packing of chromatographic columns, which provide significantly improved column performance and chromatographic separations. These methods are applicable to any of the common types of chromatographic columns, including, but not limited to, capillary columns, glass columns and stainless steel columns. With these methods columns may be prepared much more quickly than with gravity packing techniques and columns exhibit radially uniform particle packing compared to gravity packed and slurry packed columns.

Figure 1:
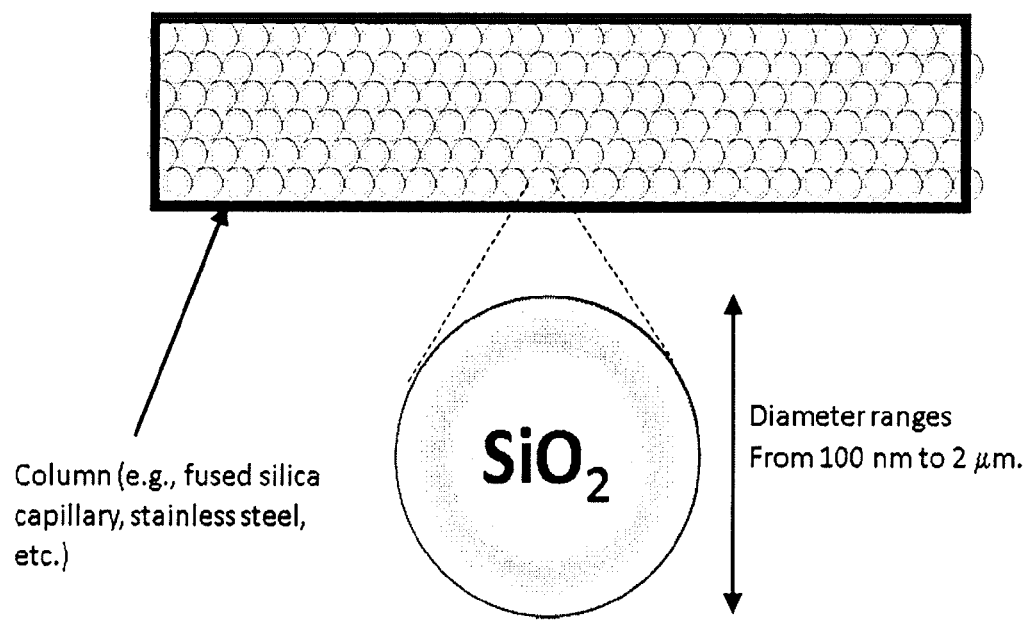
FIG. 1 is a schematic representation of a column packed with silica particles.

An ideally packed column is illustrated in FIG. 1. The chromatography medium, in this embodiment, is made of silica particles having a diameter from 100 nm to 2 μm, and they are uniformly and tightly packed in the column. Such ideal columns have been described in the scientific literature, but require several days to prepare. In addition to the long preparation time, the defect rate with traditional packing methods is high—most columns are defective. Defects include gaps between the packing material and the column wall and cracks in the material, such as those seen in the columns in FIGS. 2, 3 and 4, which were packed under gravity using conventional methods.

Figure 2:
FIG. 2 is an optical micrograph of a fused silica capillary (100 µm inner diameter) packed with 250 nm silica particles by gravity. The packed column exhibits gaps between the walls and the silica particles.
Figure 3:
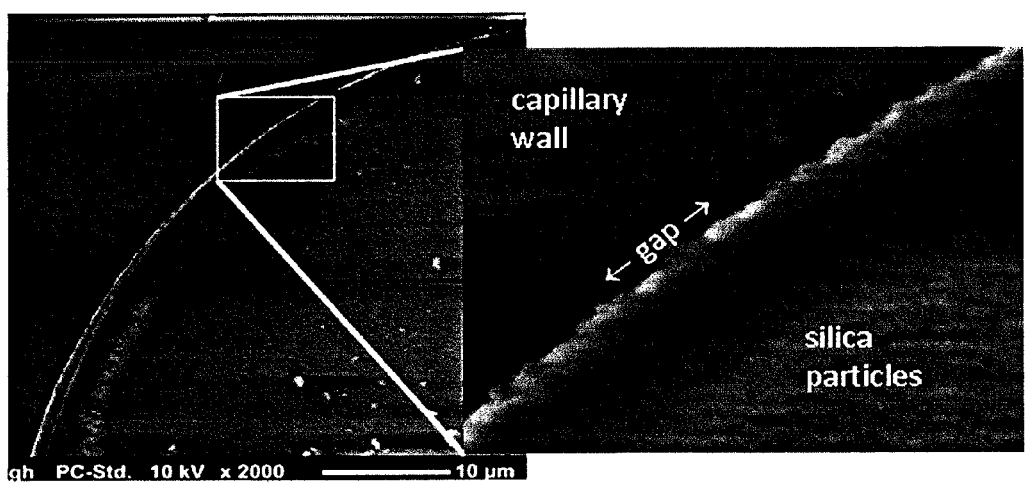
FIG. 3 is a scanning electron micrograph showing a cross-section of a packed capillary column. Gaps can be seen between the packing and the capillary wall.
Figure 4:
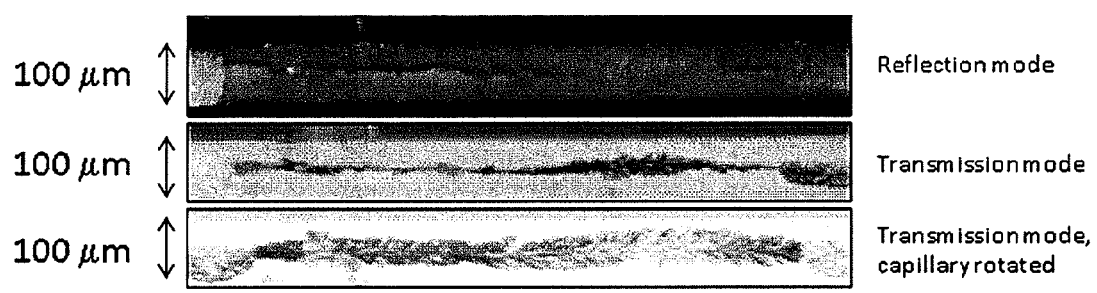
FIG. 4 presents an optical micrograph of a chromatographic column packed with 500 nm particles by gravity, illustrating another common problem, cracking along the axis of the column.

Gaps form when the forces among particles are very high, negatively affecting column performance and preventing acceptable separation of compounds in a sample. Gaps are illustrated in FIGS. 2 and 3. In column chromatography and electrophoresis, a gap between the packing and the wall creates a low resistance path out of the column, which can ruin the separation, because an analyte traveling along the wall will reach the detector at a different time than the same type of analyte traveling through the center of the column. The gap may also allow the sample material to slide out of the column, resulting in catastrophic failure of the column. Cracks can also appear in the packed material, as illustrated in FIG. 4. Cracks allow part of a chromatographic peak to take a shortcut through the column, causing catastrophic zone spreading.

Cracks and gaps can be reduced and sometimes eliminated by very slow gravitational packing over a few days. However, the described methods provide uniform packing of the separation medium, prevent gaps and cracks, and can produce useable packed columns in less than an hour instead of days.

Figure 5:
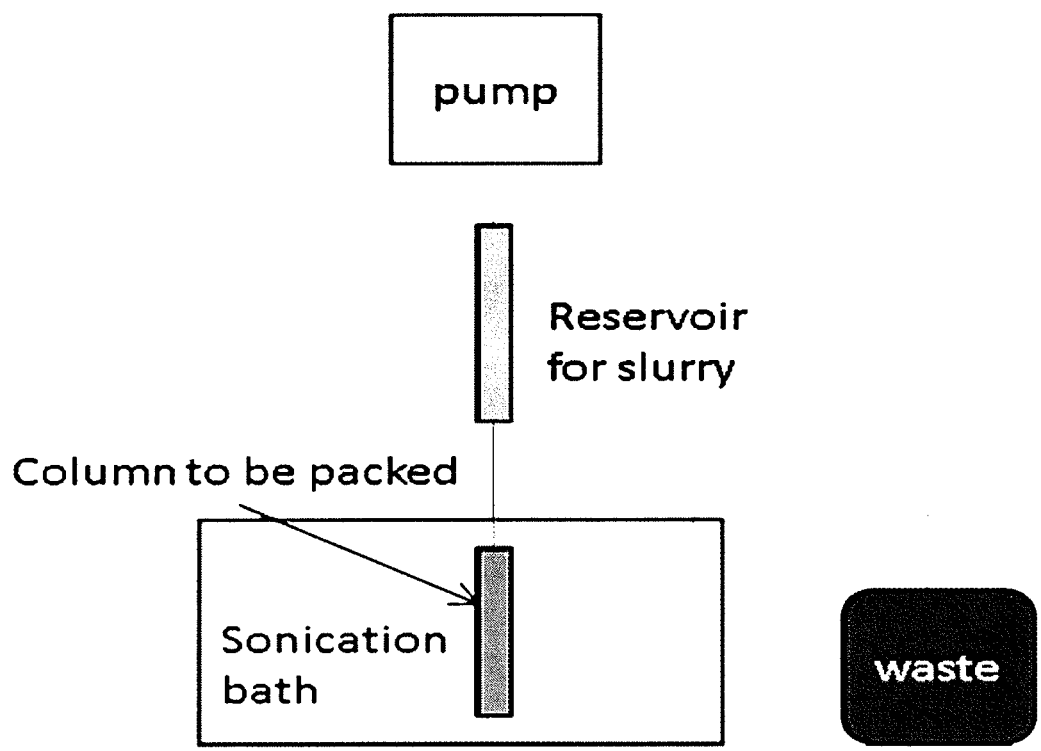
FIG. 5 is a diagram representing a configuration for packing a chromatographic column while sonicating the column.

A configuration for improved chromatographic column packing is diagrammed in FIG. 5. Generally, the column is placed in a sonication bath and packed under sonication while a slurry of silica particles is pumped from the reservoir into the column under pressure. The reservoir can be either before or after the pump, preferably after. The instrument controlling the pump can meter flow rate and report pressure, or it can meter pressure and report flow rate. This combination of sonication and pressure allows uniform packing of the chromatographic medium and leads to radial homogeneity in the packed column. We have demonstrated the packing for nonporous silica particles of a variety of diameters, ranging from 330 nm to 900 nm. However, the methods are applicable to any particle diameter that responds to sonication, i.e., spanning 100 nm to 2 μm.

In one embodiment of the methods, the reservoir is filled with the weight of particles needed for filling the column, and ultrasonication and pressure are applied simultaneously during column packing, while the flow rate is controlled and the pressure is monitored A plurality of columns can be packed simultaneously with this method by using a flow splitter and increasing the amount of packing material in the reservoir in proportion to the number of columns to be packed. The pressure reading steadily increases as packing proceeds, and the pump is stopped once the pressure levels off to a constant value. The column remains connected to the pump until the pressure dissipates to prevent a backwards pressure pushing the contents upward. Exemplary carrier solvents include 70% n-hexane and 30% isopropanol by volume for particles coated with hydrophobic monolayers, and water for hydrophilic monolayers.

Figure 6:
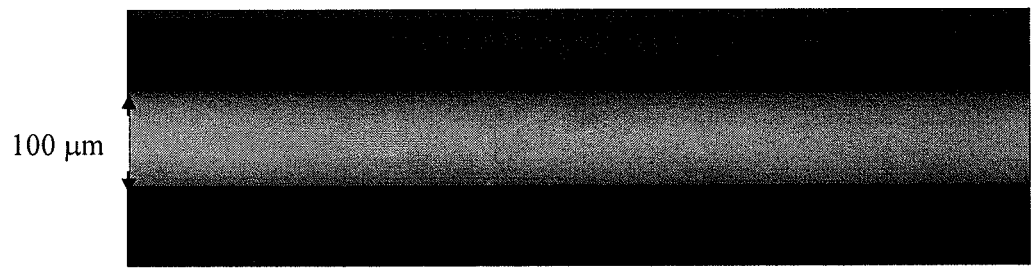
FIG. 6 is an optical micrograph of a fused silica capillary (100 µm inner diameter) packed with 150 nm silica particles using ultrasonication and applied pressure (2700× magnification). No gaps or cracks are seen in the packing or between the column wall and the packing.

By applying pressure and ultrasonication during column packing, gaps and cracks are avoided, as shown in FIG. 6, and the amount of time required to produce a useable column is dramatically reduced. For example, for a 2-cm column length, the packing may be achieved in 15 minutes or less, and for columns longer than 5 cm, the packing may be achieved in 1 hour or less. In other situations, for example, where a more viscous carrier liquid and a longer column are used, the packing may be achieved within 6 hours. Columns packed with applied pressure and ultrasonication have eddy diffusion values that are less than 1 μm, exhibiting radial homogeneity and thereby enhancing performance of the packed column.

To provide adequate pressure during column packing, the pump must exert sufficient pressure to force the particles into a dense packing. The same types of pumps widely used in packing UHPLC columns are suitable. For example, a Thermo Acela UHPLC chromatograph pump that, when set to a flow rate of 0.5 mL per minute, levels off to a pressure of 650 bar when 900 nm silica particles are packed may be used. The pressure may be programmed to ramp up to a maximum designated pressure, e.g., 1000 bar. A pressure of 200 bar is minimal for packing to occur in a reasonable amount of time, and there is no apparent upper limit in pressure that is suitable for packing the columns in conjunction with ultrasonication. In preferred embodiments, 600 or 650 bar pressure is the highest pressure reached. The Lab Alliance 1500 pump allows one to set pressure to either vary or be fixed. For particles smaller than 900 nm, it is preferred to set a maximum pressure, e.g. 650 bar, so that the pressure gradually rises during packing, and once the pressure reaches 650 bar, the pressure remains constant and the flow rate gradually decreases. Once the flow rate reaches a constant value, the column is considered to be packed. Needlessly high pressure raises the possibility of leaks, hence the value of setting a maximum pressure.

Ultrasonication, also referred to as sonication, opposes the packing effects of applied pressure by forcing the packing material particles apart. As a result, particles are not only densely packed, but are also evenly spaced. Any appropriate sonicator may be used to pack the column. Appropriate commercially-available sonicators come in a range of sizes and generally operate at 20 kHz or 10 kHz and between 10 and 300 watts. For example, a suitable ultrasonicator is a VWR B2500A MT, which is commonly used in laboratories to clean glassware and laboratory instruments. Other appropriate ultrasonicators currently on the market include the Bandelin Ultrasonicator, the Mettler Sonicator Ultrasound 730, and the Fisher FS5, L&R bath sonicator.

The column to be packed may be any suitable chromatographic column, including, but not limited to fused silica, glass, ceramic, stainless steel, aluminum, PEEK, acrylic, or polystyrene chromatography columns. The inner column diameters may vary and a range of diameters are suitable, depending on the desired use of the column. For example, the column may have an inner diameter ranging from 10 μm to 1 meter, and preferably 25 μm to 5 cm. Fused silica capillary columns have inner diameters ranging from 10 μm to 500 μm. The packing material may be any suitable chromatographic separation material, including, but not limited to, silica, silane-treated silica, polystyrene particles, nonporous silica particles, porous silica particles and core-shell silica particles. The particles can be spherical or irregular in shape.

Chromatographic applications include size exclusion, ion-exchange, affinity, hydrophilic interaction, perfusion, and reverse phase liquid chromatography for the separation of small molecules, peptides, sugars and polysaccharides, glycans, monoclonal antibodies, proteins and other macromolecular compounds, and combinations thereof. The columns are suitable for high pressure liquid chromatography (HPLC), ultraperformance liquid chromatography (UHPLC), fast protein liquid chromatography (FPLC), and ultrafiltration, and may also be used to separate compounds by electrophoresis, isoelectric focusing and capillary electrochromatography. Selection of a separation material depends on the intended use of the column and the size of the sample. The particles of the separation material may range in size from 100 nm to 10 µm, preferably 300 nm to 2 µm, most preferably 300 nm to 900 nm.

A review of conventional column packing methods is found in *J. Sep. Sci.* 27: 1475-1482, 2004. Conventional packing of columns may employ sonication to suspend the particles as a slurry into a carrier solvent, but pressure alone is used during packing (*Anal. Chem.* 60: 1662-1665, 1988). Sonication of the entire column during packing, as described herein, has not previously been reported for submicrometer particles or for a liquid carrier.

EXAMPLES

Packing material used in the following examples was obtained from Fiberoptic Center, Inc. (AngstromSphere Silica Spheres, #SIOP025-01, #SIOP050-01 and #SIOP0100-01), and from Nanogiant, LLC. A wide range of chromatographic packing material is commercially available and known in the art. Chemical modifications include, but are not limited to, hydrocarbon monolayers, anion and cation exchange groups, polar groups, and hydrophilic interaction phases.

Example 1

Silica Capillary Column Prepared with Ultrasonication and Pressure

A fused silica capillary column having a 100 µm inside diameter and length of 2 cm was packed with 150 nm silica particles. Pressure and ultrasonication were applied simultaneously using a Thermo Scientific Accela pump and VWR sonicator. An optical micrograph of a column prepared by this method is shown in FIG. 6. The small particle size makes the capillary translucent to allow visual inspection of the entire volume of the packed capillary. No gaps between the capillary wall and the silica particles and no cracking in the packed material are observed.

Figure 7:
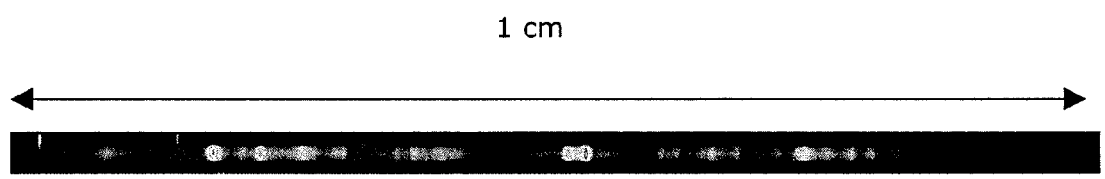
FIG. 7 shows a rapid isoelectric focusing separation of the glycoforms of prostate specific antigen over a 1-cm distance in a 3-cm long capillary of 75 µm i.d., packed with 700 nm silica particles whose surfaces were modified with a polyacrylamide layer.

A 3 cm long capillary packed by the same method, but with 900 nm particles also exhibited no visual gaps or cracks. The capillary column was used for fast isoelectric focusing of glycoforms of prostate specific antigen (PSA) that had been labeled with a dye that conserves the charge, as illustrated in FIG. 7. These results show that the improved packing method can assist in the discovery of new cancer biomarkers.

Example 2

Capillary Column Packed Under Gravitational Pressure

A fused silica capillary column with an inner diameter of 100 µm and length of 2 cm was packed with 250 nm diameter silica particles using gravity packing over 3 days. As shown in FIG. 2, the column exhibits gaps between the silica and the capillary wall. Typical scanning electron micrographs of capillaries prepared with this method show gaps between the capillary wall and the packing material, as illustrated in FIG. 3.

Example 3

Stainless Steel Column Packed Using Simultaneous Ultrasonication and Pressure

Figure 8:
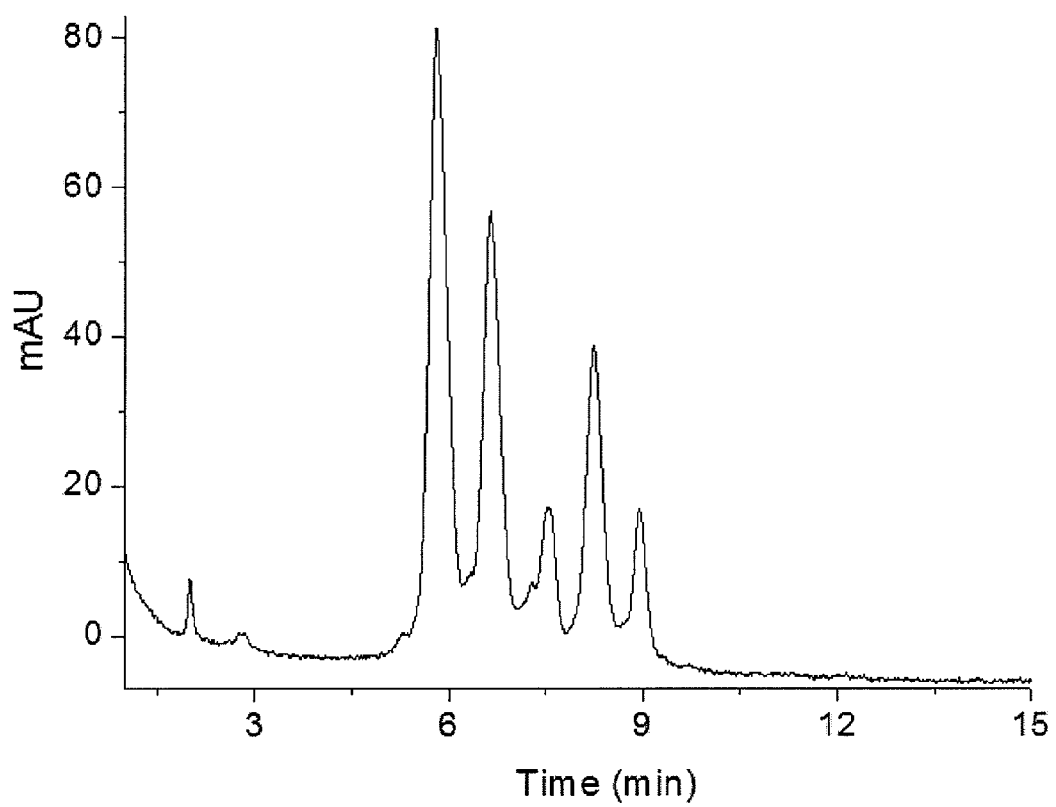
FIG. 8 shows a UHPLC separation of ribonuclease B glycoforms that differ from those in adjacent peaks by only one mannose group. The separation was performed using a 2-cm long stainless steel column of 2.1 mm i.d., packed with 700 nm particles bearing a surface modification of polyacrylamide groups.

A 2 cm long, 2.1 mm i.d. column was connected through tubing to a reservoir, and the empty column was immersed in an ultrasonic bath (VWR B2500A MT). A slurry of 750 nm silica particles bearing a layer of polyacrylamide in water was held in a reservoir preceding the column to be packed. A Lab Alliance pump was used to push the slurry into the column and pack the chromatography material under 600 bar of pressure. The column was packed in 35 minutes. The column was used to separate glycoforms of ribonuclease B, which differ from one another by only a single mannose group. These results are shown in FIG. 8. The separation was achieved by hydrophilic interaction chromatography, and performance exceeded that seen with commercially available columns as indicated by the resolution.

Example 4

Capillary Column Packed with Using Ultrasonication and Pressure

Figure 9:
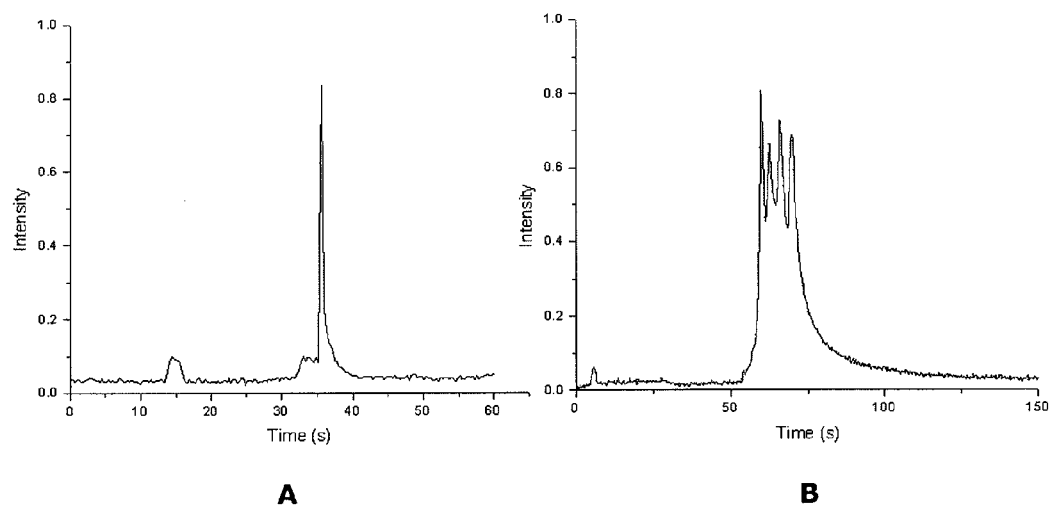
FIG. 9 shows a UHPLC separation of a monoclonal antibody(anti-PSA) using a packed 2 cm long fused silica capillary having an inner diameter of 75 µm. The column was packed using simultaneous ultrasonication and pressure with 500 nm nonporous silica particles that had been reacted to form a monolayer of n-butyl groups on the particles. A. Original antibody; B. Oxidized antibody. The original antibody exhibits a theoretical plate height of only 600 nm, with a contribution from eddy diffusion that is less than 100 nm.

A capillary 2-cm long with an i.d. of 75 µm was packed with 500 nm particles bearing a butyl monolayer using simultaneous ultrasonication and pressure. Extremely sharp peaks for reversed-phase isocratic UHPLC of A) a monoclonal antibody to PSA, and B) the oxidized antibody, were obtained as shown in FIG. 9. The height equivalent to a theoretical plate, which can best be measured for an isolated peak, is calculated for the peak in part A to be 600 nm, and the eddy diffusion term is smaller than 100 nm for this column.

What is claimed:

1. A method for packing a chromatographic column comprising silica particles, the method comprising the steps of
   a) introducing the silica particles into the chromatographic column, wherein the chromatographic column has a length of 2 to 10 cm and an inner diameter of 25 µm to 5 cm, and the silica particles have a diameter of 100 nm to 900 nm;
   b) ultrasonicating the chromatographic column; and
   c) applying pressure to the silica particles,
   wherein steps a)-c) are performed simultaneously and wherein a packed chromatographic column with an eddy diffusion term of less than 1 µM is formed, wherein the silica particles are uniformly packed and exhibit no cracks or uninterrupted contact between the inner surface of the column and the silica particles, and wherein the packed chromatographic column is suitable for HPLC, UHPLC, or FPLC.

2. The method of claim 1, wherein the silica particles have a diameter range from about 150 nm to 900 nm.

3. The method of claim 1, wherein the silica particles comprise nonporous silica particles, porous silica particles, core-shell silica particles, or combinations thereof.

4. The method of claim 1, wherein the chromatographic column comprises fused silica, glass, ceramic, stainless steel, aluminum, PEEK, acrylic, or polystyrene.

5. The method of claim 4, wherein the chromatographic column comprises fused silica.

6. The method of claim 4, wherein the chromatographic column comprises glass.

7. The method of claim 4, wherein the chromatographic column comprises stainless steel.

8. The method of claim 1, wherein a plurality of chromatographic columns are packed simultaneously.

9. The method of claim 1, wherein the chromatographic column is packed in 6 hours or less.

10. The method of claim 9, wherein the chromatographic column is packed in 1 hour or less.

11. The method of claim 1, wherein the pressure is applied within a range from about 200 bar to about 1,000 bar.

12. A packed chromatographic column comprising:
(i) a chromatographic column having a length of 2 to 10 cm and an inner diameter of 25 µm to 5 cm, and
(ii) silica particles inside the chromatographic column, wherein the silica particles have a diameter of 100 nm to 900 nm,
the packed chromatographic column prepared by the steps of
a) introducing the silica particles into the chromatographic column;
b) ultrasonicating the chromatographic column; and
C) applying pressure to the silica particles,
wherein steps a)-c) are performed simultaneously,
wherein the packed chromatographic column has an eddy diffusion term of less than 1 µm;
wherein the silica particles are uniformly packed and exhibit no cracks or uninterrupted contact between the inner surface of the chromatographic column and the silica particles; and
wherein the packed chromatographic column is suitable for HPLC, UHPLC or FPLC.

13. The packed chromatographic column of claim 12, wherein the chromatographic column comprises a glass capillary column comprising an inner diameter of about 25 µm, a length of about 10 cm, and the silica particles have a diameter within the range of 100 nm to 900 nm wherein the packed chromatographic column is suitable for separating proteins.

14. The packed chromatographic column of claim 12, wherein the chromatographic column is a stainless steel chromatographic column, a fused silica chromatographic column or a PEEK chromatographic column.

15. The packed chromatographic column of claim 12, wherein the chromatographic column comprises a fused silica capillary column comprising an inner diameter of about 75 µm, a length of about 5 cm, and the silica particles have a diameter of 750 nm, wherein the packed chromatographic column is suitable for isoelectric focusing of proteins.

16. The packed chromatographic column of claim 12, wherein the chromatographic column comprises a fused silica capillary column comprising an inner diameter of about 75 µm, a length of about 5 cm, and the silica particles have a diameter of 750 nm, wherein the packed chromatographic column is suitable for hydrophilic interaction chromatography of proteins and peptides.

17. The packed chromatographic column of claim 12, wherein the chromatographic column comprises a fused silica capillary column comprising an inner diameter of about 75 µm, a length of about 5 cm, and, the silica particles have a diameter of 750 nm, wherein the packed chromatographic column is suitable for reversed phase chromatography of proteins and peptides.

18. The packed chromatographic column of claim 12, wherein the column has a length of 3 to 5 cm.

19. The packed chromatographic column of claim 12, wherein the column has an inner diameter of 75 µm to 5 cm.

20. The packed chromatographic column of claim 12, wherein the column has an inner diameter of 2.1 mm.

21. The packed chromatographic column of claim 12, wherein the silica particles have a diameter of 150 nm to 900 nm.

22. The packed chromatographic column of claim 12, wherein the silica particles have a diameter of 300 nm to 900 nm.

23. A packed chromatographic column comprising silica particles inside a column, wherein the silica particles have a diameter of 100 nm to 150 nm, the packed chromatographic column prepared by the steps of
a) introducing the silica particles into the column;
b) ultrasonicating the column; and
c) applying pressure to the silica particles,
wherein steps a)-c) are performed simultaneously,
wherein the packed chromatographic column has an eddy diffusion term of less than 1 µm;
wherein the silica particles are uniformly packed and exhibit no cracks or uninterrupted contact between the inner surface of the column and the silica particles, and
wherein the packed chromatographic column is suitable for HPLC, UHPLC or FPLC.

24. A packed chromatographic column comprising silica particles inside a column, the packed chromatographic column prepared by the steps of
a) introducing the silica particles into the column;
b) ultrasonicating the column; and
c) applying pressure to the silica particles,
wherein steps a)-c) are performed simultaneously,
wherein the packed chromatographic column has an eddy diffusion term of less than 100nm;
wherein the silica particles are uniformly packed and exhibit no cracks or uninterrupted contact between the inner surface of the column and the silica particles, and
wherein the packed chromatographic column is suitable for HPLC, UHPLC or FPLC.

* * * * *